United States Patent
Mine et al.

(10) Patent No.: US 10,653,655 B2
(45) Date of Patent: May 19, 2020

(54) COMPOSITION FOR PREVENTING OR IMPROVING PERIPHERAL NEUROPATHY

(71) Applicant: AJINOMOTO CO., INC., Tokyo (JP)

(72) Inventors: Tomoyuki Mine, Kawasaki (JP); Ryo Uchida, Kawasaki (JP); Naoki Hayashi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/129,875

(22) Filed: Sep. 13, 2018

(65) Prior Publication Data

US 2019/0008814 A1    Jan. 10, 2019

Related U.S. Application Data

(60) Division of application No. 15/298,953, filed on Oct. 20, 2016, now abandoned, which is a continuation of application No. PCT/JP2015/062092, filed on Apr. 21, 2015.

(30) Foreign Application Priority Data

Apr. 22, 2014  (JP) ................................ 2014-088051

(51) Int. Cl.
*A61K 31/202* (2006.01)
*A61K 31/198* (2006.01)
*A61K 35/60* (2006.01)

(52) U.S. Cl.
CPC .......... *A61K 31/202* (2013.01); *A61K 31/198* (2013.01); *A61K 35/60* (2013.01)

(58) Field of Classification Search
None
See application file for complete search history.

(56) References Cited

U.S. PATENT DOCUMENTS 7,897,641 B2    3/2011    Cavazza

FOREIGN PATENT DOCUMENTS

| CN | 1281716 | 7/1999 | |
|---|---|---|---|
| WO | WO 2005/023271 A1 | 3/2005 | |
| WO | WO 2011/111355 A1 | 9/2011 | |
| WO | WO-2011111355 A1 * | 9/2011 | ........... A61K 31/198 |

OTHER PUBLICATIONS

Ghoreishi et al. (BMC Cancer, 12:355, 2012, 1-8) (Year: 2012).*
Guidance for Industry (Estimating the Maximum Safe Starting Dose in Initial Clinical Trails for Therapeutics in Adult Healthy Volunteers, Jul. 2005) (Year: 2005).*
International Search Report dated Jun. 23, 2015 in PCT/JP2015/062092.
Reto Savoca, et al., "Effects of L-serine on neurons in vitro", Journal of Neuroscience Methods, vol. 61, 1995, pp. 159-167.
Junya Mitoma, et al., "A novel metabolic communication between neurons and astrocytes: non-essential amino acid L-serine released from astrocytes is essential for developing hippocampal neurons", Neuroscience Research, vol. 30, 1998, pp. 195-199.
Shigeki Furuya, et al., "L-Serine and glycine serve as major astroglia-derived trophic factors for cerebellar Purkinje neurons", Proc. Natl. Acad. Sci., USA, vol. 97, No. 21, 2000, pp. 11528-11533.
T. Kiya et al., "Role of Satellite Cell-Derived L-Serine in the Dorsal Root Ganglion in Paclitaxel-Induced Painful Peripheral Neuropathy", Neuroscience, vol. 174, 2011, pp. 190-199.
Haim Shapiro, "Could n-3 polyunsaturated fatty acids reduce pathological pain by direct actions on the nervous system?", Prostaglandins, Leukotrienes and Essential Fatty Acids, 2003, vol. 63. No. 3, pp. 219-224.
Zohreh Ghoreishi, et al. "Omega-3 fatty acids are protective against paclitaxel-induced peripheral neuropathy: A randomized double-blind placebo controlled trial", BMC Cancer, 12:355, 2012, pp. 1-8.
Extended European Search Report dated Nov. 22. 2017 in Patent Application No. 15783692.5.
Office Action dated Feb. 12, 2019 in Japanese Patent Application No. 2016-514944, 4 pages (submitting English translation only).
Kawamata, T. et al. "Role of satellite cell-derived L-serine in the dorsal root ganglion in paclitaxel-induced peripheral neuropathy" Folia Pharmacologica Japonica, vol. 141. No. 2, 2013, pp. 71-75.

* cited by examiner

*Primary Examiner* — Daniel M Podgorski
(74) *Attorney, Agent, or Firm* — Oblon, McClelland, Maier & Neustadt, L.L.P.

(57) ABSTRACT

Compositions which contain an amino acid containing serine and a lipid containing a n-3 fatty acid are useful for the prophylaxis or improvement of peripheral neuropathy.

14 Claims, 11 Drawing Sheets

COMPOSITION FOR PREVENTING OR IMPROVING PERIPHERAL NEUROPATHY

CROSS REFERENCES TO RELATED APPLICATIONS

This application is a divisional of U.S. application Ser. No. 15/298,953, filed on Oct. 20, 2016, which is a continuation of International Patent Application No. PCT/JP2015/062092, filed on Apr. 21, 2015, and claims priority to Japanese Patent Application No. 2014-088051, filed on Apr. 22, 2014, each of which is incorporated herein by reference in their entireties.

BACKGROUND OF THE INVENTION

Field of the Invention

The present invention relates to compositions which are useful for the prophylaxis or improvement of peripheral neuropathy. The present invention also relates to methods for the prophylaxis or improvement of peripheral neuropathy.

DISCUSSION OF THE BACKGROUND

Pain is classified into "neuropathic", "nociceptive", and "psychogenic" pain, and these three types of pain act independently or compositely to cause a pain. "Neuropathic" pain easily becomes chronic, and shows different characteristics from "nociceptive" pain including many acute pains (e.g., injury, burn, etc.). Acute pain, which follows damage to body tissue, functions as an alert of body tissue damage and leads to the repair of the body tissue in a given period. On the other hand, chronic pain does not act as a defensive biological function, and is considered to last for several months to several years or longer (see Neurological Therapeutics, vol. 27, No. 4, p 591-622 (2010) which is incorporated herein by reference in its entirety).

According to a major research study relating to pain, about 23% of Japanese adults have a chronic pain, and 70% thereof fail to appropriately alleviate the pain (see Clinical Orthopaedic Surgery, vol. 47, No. 2, p 127-134 (2012) which is incorporated herein by reference in its entirety). Since psychological anxiety and melancholiness associated with pain have a high impact on the limitation of activity, removal of pain improves quality of life.

Pain due to peripheral neuropathy is pain caused by a primary damage or dysfunction of some part of the peripheral neurotransmitter system. The main factors of this neuropathy are trauma or injury etc. of peripheral nerve, plexus or perineural soft tissue. Pain due to peripheral neuropathy is also developed by injury of the central somatosensory pathway (e.g., ascending somatosensory pathway in the spinal cord, brain stem, thalamus or cortex). Pain due to peripheral neuropathy is also induced by any of, for example, neurodegenerative disease, bone degenerative disease, metabolism abnormality disease, cancer, infection, inflammation, after surgery, trauma, radiation treatment, treatment with anticancer agent and the like.

Loss of muscle strength, aging, obesity, and the like in elderly people triggers a decrease in the function of knee joint, which in turn induces loose engagement, deformation and rupture of knee cartilage and meniscus. In some cases, such loose engagement, deformation and rupture of knee cartilage and meniscus occur since knee cartilage and meniscus that function as a cushion of knee joint wear away by small portions due to activities over a long period and are deformed, while in other cases they occur due to disease, injury and the like such as rheumatoid arthritis, knee injury and the like. In many of these cases, over-retention of synovial fluid occurs due to inflammation and causes pain. Also, hypofunction triggered by loss of muscle strength, aging, obesity and the like in elderly people may occur in the waist having cartilage as in the knees. It induces looseness, deformation or rupture of engagement in the waist part, which often accompanies chronic pain.

In cancer patients, unbearable numbness, ache and the like last for a long time due to oppression of peripheral nerve and spinal cord by tumor, tissue infiltration, or peripheral neuropathy and the like by the action of chemotherapy itself. Particularly, pain caused by chemotherapy often forces the chemotherapy to be stopped, and pain in the chemotherapy forms a large obstacle to the cancer treatment (see Folia Pharmacol. Jpn., 136, p 275-279 (2010) which is incorporated herein by reference in its entirety).

Peripheral neuropathy is characterized by a hyperesthesia response (allodynia) wherein a pain is felt by a stimulation, which is not felt by healthy people. While the molecular mechanism of the onset thereof has not been completely clarified, abnormal responses such as hyperexcitability, sustained spontaneous excitation and the like occur in sensory neuron, as commonly seen in various peripheral neuropathies.

Peripheral neuropathic pain is being treated symptomatically with opioid central analgesics such as morphine and the like; steroid; non-steroidal antiphlogistic analgetic; vitamin and the like; however, the side effects are strong and a sufficient effect is not obtained (see Neurological Therapeutics, vol. 27, No. 4, p 591-622 (2010) which is incorporated herein by reference in its entirety). Therefore, a method capable of relieving the peripheral neuropathic pain effectively with fewer side effects is desired.

Serine is one kind of non-essential amino acid, and is involved in biosynthesis of nucleic acids such as purine, pyrimidine and the like, and biosynthesis of cysteine. In addition, the involvement of serine in elongation promotion of the neurite of dorsal root ganglion of chicken embryonic cell, and survival and growth of hippocampus neuron derived from fetal rat cell and cerebellar Purkinje neuron derived from fetal rat has been reported (see J. Neurosci. Methods, 61, p 159-167 (1995); Neurosci. Res. 30, p 195-199 (1998); and Proc. Natl. Acad. Sci. USA, 97, p 11528-11533 (2000) all of which are incorporated herein by reference in their entireties). However, all of these reports are in vitro evaluations in the initial process of nerve cell development, and the situation is vastly different from that of peripheral neuropathy after formation of nerve cell.

WO 2011/111355, which is incorporated herein by reference in its entirety, reports that L-serine shows a relieving effect on peripheral neuropathic pain in an animal model of anticancer agent or diabetes. Anticancer agents and diabetes directly influence peripheral nerve cell and nerve axon. However, peripheral neuropathic pain due to gonitis is a pain topically acting on the sensory organ of knee, and the nature of this pain is different from that of pain caused by anticancer agents or diabetes. Peripheral neuropathic pain due to gonitis is not studied in WO 2011/111355. The relieving effect of L-serine on peripheral neuropathic pain due to anticancer agents and diabetes, which was studied in WO 2011/111355, was partial even at the maximum concentration of L-serine.

On the other hand, while eicosapentaenoic acid among n-3 fatty acids is already in clinical use as a hypertriglyceridemia improving agent, there is no clear clinical report relating to pain relief. In a test using an animal model, a clear relieving effect on the mechanical stimulation on the peripheral nerve has not been reported even when eicosapentaenoic acid was added to meal and taken by the animal model.

As mentioned above, as the situation stands, a medical preparation, a food or a supplement containing serine and n-3 fatty acid, which has a function to prevent or improve peripheral neuropathic pain, has not been provided.

SUMMARY OF THE INVENTION

Accordingly, it is one object of the present invention to provide novel compositions having a prophylactic or improvement effect on peripheral neuropathy.

It is another object of the present invention to provide novel methods for the prophylaxis or improvement of peripheral neuropathy.

These and other objects, which will become apparent during the following detailed description, have been achieved by the inventors' discovery that peripheral neuropathy can be prevented or improved by a combination of serine and a n-3 fatty acid.

Accordingly, the present invention is as described below.

(1) A composition for the prophylaxis or improvement of peripheral neuropathy, which comprises an amino acid comprising serine, and a lipid comprising n-3 fatty acid.

(2) The composition of (1), wherein the n-3 fatty acid comprises one or more kinds selected from the group consisting of eicosapentaenoic acid, docosapentaenoic acid and docosahexaenoic acid.

(3) The composition of (1) or (2), wherein the amount of serine is not less than 50 wt % relative to the total amount of amino acid.

(4) The composition of any of (1) to (3), which is (1) substantially free of threonine, or has (2) a weight ratio of serine relative to threonine of not less than 2.60.

(5) The composition of any of (1) to (4), wherein the amount of n-3 fatty acid is not less than 20 wt % relative to the total amount of the lipid.

(6) The composition of any of (1) to (5), which has a unit package form per single intake, and comprises not less than 0.1 g of serine in one unit, and not less than 0.03 g of n-3 fatty acid in one unit.

(7) The composition of any of (1) to (6), wherein the peripheral neuropathy is any one kind selected from the group consisting of peripheral neuropathy due to an anticancer agent, peripheral neuropathy due to knee osteoarthritis, backbone neuropathy, peripheral neuropathy due to mechanical compression of peripheral nerve trunk, diabetic peripheral neuropathy, renal disease uremic peripheral neuropathy, peripheral neuropathy due to herpes zoster and Guillain-Barre syndrome.

(8) The composition of any of (1) to (6), wherein the peripheral neuropathy is peripheral neuropathy due to an anticancer agent or peripheral neuropathy due to knee osteoarthritis.

(9) A composition for the prophylaxis or improvement of activity decline due to peripheral neuropathy, which comprises an amino acid comprising serine, and a lipid comprising n-3 fatty acid.

(10) The composition of any of (1) to (9), which is a medicament.

(11) A method for the prophylaxis or improvement of peripheral neuropathy, comprising administering an effective amount of a composition comprising an amino acid comprising serine, and a lipid comprising n-3 fatty acid to a subject in need thereof.

(12) The method of (11), wherein the n-3 fatty acid comprises one or more kinds selected from the group consisting of eicosapentaenoic acid, docosapentaenoic acid and docosahexaenoic acid.

(13) The method of (11) or (12), wherein the amount of serine in the composition is not less than 50 wt % relative to the total amount of amino acid in the composition.

(14) The method of any of (11) to (13), wherein (1) the composition is substantially free of threonine, or (2) the composition has a weight ratio of serine relative to threonine of not less than 2.60.

(15) The method of any of (11) to (14), wherein the amount of n-3 fatty acid in the composition is not less than 20 wt % relative to the total amount of the lipid in the composition.

(16) The method of any of (11) to (15), wherein the composition has a unit package form per single intake, comprises not less than 0.1 g of serine in one unit, and not less than 0.03 g of n-3 fatty acid in one unit.

(17) The method of any of (11) to (16), wherein the peripheral neuropathy is any one kind selected from the group consisting of peripheral neuropathy due to an anticancer agent, peripheral neuropathy due to knee osteoarthritis, backbone neuropathy, peripheral neuropathy due to mechanical compression of peripheral nerve trunk, diabetic peripheral neuropathy, renal disease uremic peripheral neuropathy, peripheral neuropathy due to herpes zoster and Guillain-Barre syndrome.

(18) The method of any of (11) to (16), wherein the peripheral neuropathy is peripheral neuropathy due to an anticancer agent or peripheral neuropathy due to knee osteoarthritis.

(19) A method for the prophylaxis or improvement of activity decline due to peripheral neuropathy, comprising administering an effective amount of a composition comprising an amino acid comprising serine, and a lipid comprising n-3 fatty acid to a subject in need thereof.

(20) A composition comprising an amino acid comprising serine, and a lipid comprising n-3 fatty acid, which is for use for the prophylaxis or improvement of peripheral neuropathy.

(21) The composition of (20), wherein the n-3 fatty acid comprises one or more kinds selected from the group consisting of eicosapentaenoic acid, docosapentaenoic acid and docosahexaenoic acid.

(22) The composition of (20) or (21), wherein the amount of serine is not less than 50 wt % relative to the total amount of amino acid.

(23) The composition of any of (20) to (22), which is (1) substantially free of threonine, or has (2) a weight ratio of serine relative to threonine of not less than 2.60.

(24) The composition of any of (20) to (23), wherein the amount of n-3 fatty acid is not less than 20 wt % relative to the total amount of the lipid.

(25) The composition of any of (20) to (24), which has a unit package form per single intake, and comprises not less than 0.1 g of serine in one unit, and not less than 0.03 g of n-3 fatty acid in one unit.

(26) The composition of any of (20) to (25), wherein the peripheral neuropathy is any one kind selected from the group consisting of peripheral neuropathy due to an anticancer agent, peripheral neuropathy due to knee osteoarthritis, backbone neuropathy, peripheral neuropathy due to mechanical compression of peripheral nerve trunk, diabetic peripheral neuropathy, renal disease uremic peripheral neuropathy, peripheral neuropathy due to herpes zoster and Guillain-Barre syndrome.

(27) The composition of any of (20) to (25), wherein the peripheral neuropathy is peripheral neuropathy due to an anticancer agent or peripheral neuropathy due to knee osteoarthritis.

(28) A composition comprising an amino acid comprising serine, and a lipid comprising n-3 fatty acid, which is for use for the prophylaxis or improvement of activity decline due to peripheral neuropathy.

(29) The composition of any of (20)-(28), which is a medicament.

According to the present invention, the composition for the prophylaxis or improvement of peripheral neuropathy can be provided. Particularly, the composition provides an effect of relieving peripheral neuropathic pain, and is useful for peripheral neuropathy due to administration of anticancer agents, peripheral neuropathy due to knee osteoarthritis, backbone neuropathy (e.g., hernia of intervertebral disk, lumbar spinal stenosis, spondylosis deformans etc.), peripheral neuropathy due to mechanical compression of peripheral nerve trunk, diabetic peripheral neuropathy, renal disease uremic peripheral neuropathy, peripheral neuropathy due to herpes zoster and Guillain-Barre syndrome and the like. The composition can also prevent or improve activity decline due to peripheral neuropathy. Furthermore, since the composition contains serine and n-3 fatty acid with established safety as active ingredients, it can be ingested safely for a long term, and can enhance the QOL of the subject who ingests.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
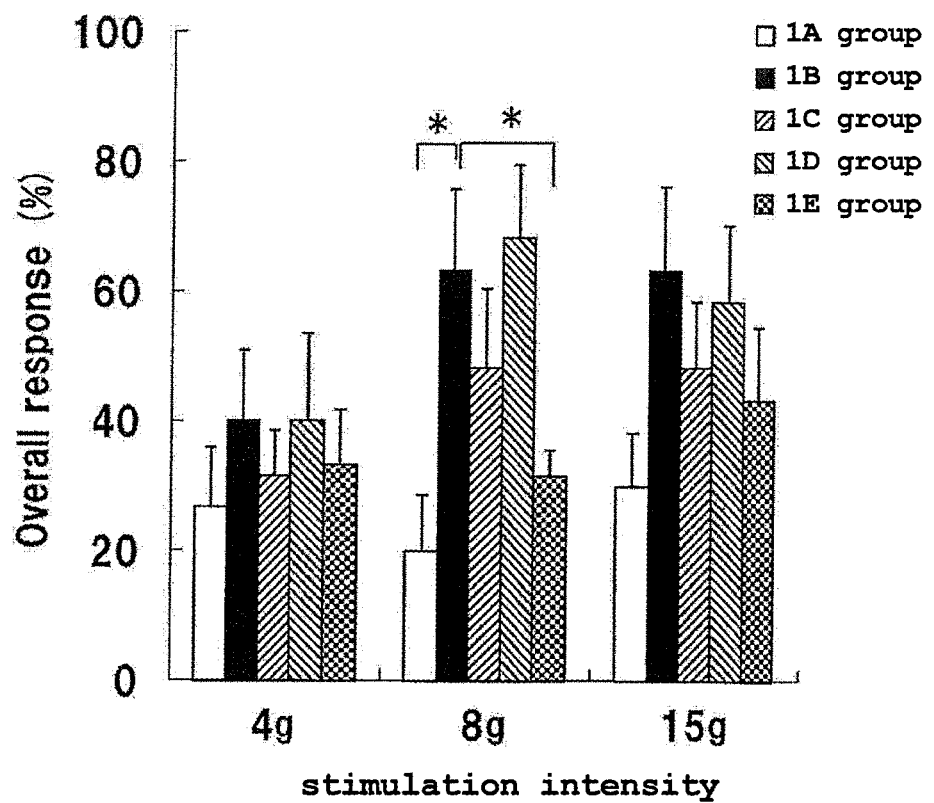
FIG. 1 shows the results of Von Frey test at 22 days after the start of the administration of an anticancer agent in Experimental Example 1. * shows the presence of a significant difference ($p<0.05$, non-paired t-test) as compared to 1B group. The vertical axis (Overall response (%)) shows the ratio (%) of the number of pain response relative to the number of pressing of a filament.

The composition for the prophylaxis or improvement of peripheral neuropathy of the present invention (hereinafter to be also simply referred to as "the composition of the present invention") is mainly characterized in that it contains an amino acid comprising serine, and a lipid comprising n-3 fatty acid.

In the present specification, the "prophylaxis" of peripheral neuropathy means prevention of exteriorization of various symptoms of peripheral neuropathy (e.g., hypersensitive pain, paresthesia, numbness in limbs etc.) (also including prevention of recurrence) in an individual who does not show the symptoms. The "improvement" of peripheral neuropathy means relief of various symptoms of peripheral neuropathy, or prevent or delay exacerbation of the symptoms, in an individual who shows the symptoms.

Amino Acid Comprising Serine

An amino acid used in the present invention essentially contains serine. While the form of serine is not particularly limited, it may be any of a free form, amino acid constituting a peptide and amino acid constituting a protein. When free serine is used, it may be a salt or any form of the solvated thereof, or a mixture of these.

Examples of the salt of serine include acid addition salt, salt with base and the like, and a physiologically acceptable salt is preferable.

Examples of the acid that forms a physiologically acceptable salt of serine include inorganic acids such as hydrogen chloride, hydrogen bromide, sulfuric acid, phosphoric acid and the like; and organic acids such as acetic acid, lactic acid, citric acid, tartaric acid, maleic acid, fumaric acid, monomethyl sulfuric acid and the like.

Examples of the base that forms a physiologically acceptable salt of serine include inorganic bases such as hydroxide or carbonate of metal (e.g., sodium, potassium, calcium etc.), ammonia and the like; and organic bases such as ethylenediamine, propylenediamine, ethanolamine, monoalkylethanolamine, dialkylethanolamine, diethanolamine, triethanolamine and the like.

A salt of only one kind of these salts or two or more kinds of salts in combination may be used.

Serine in a free form to be used in the present invention may be any of L-form, D-form and DL-form, and L-form is preferable.

The production method of serine is not particularly limited, and a method known per se (e.g., protein hydrolysis method, chemical synthesis method, enzyme method, fermentation method etc.) can be used for production. A commercially available product may also be used. Serine can also be obtained by enzymatic hydrolysis of an animal or plant-derived natural protein having an amino acid sequence containing the serine residue.

The composition of the present invention may contain, in addition to serine, an amino acid other than serine (e.g., threonine, glycine etc.). The form of these amino acids is not particularly limited, and may be a free form and a salt thereof, or a form of peptide wherein two or more amino acids are linked by a peptide bond. Also, it may have a form of a protein, and examples of the protein include animal-derived protein (e.g., casein, acid casein, casein sodium, casein calcium, whey protein, milk serum whey protein, fish meat protein, egg protein, and these hydrolysate etc.) and plant-derived protein (e.g., soybean protein, wheat protein, corn protein, and these hydrolysate etc.) and the like. The amino acid to be used for the composition of the present invention may be any of L-form, D-form and DL-form.

The amount of serine in the composition of the present invention is preferably not less than 50 wt %, more preferably not less than 70 wt %, particularly preferably not less than 90 wt %, relative to the total amount of amino acid. The amount of serine in the composition of the present invention is calculated as a total weight of serine in any form contained in the composition of the present invention. When the form of serine is other than a free form, for example, salt or amino acid constituting peptide and protein, and the like, the weight of the serine is converted to the weight of a free form. The "total amount of amino acid" is calculated as a total weight of amino acid in any form (e.g., free amino acid and a salt thereof, peptide, protein etc.) contained in the composition of the present invention. When the form of amino acid is other than a free form, for example, salt or peptide and protein, and the like, the weight of the amino acid is converted to the weight of a free form.

While the upper limit of the amount of serine in the composition of the present invention is not particularly limited, it is generally 100 wt %, preferably 95 wt %, relative to the total amount of amino acid.

When the amino acid used in the present invention contains threonine, the weight ratio of serine to threonine (serine/threonine) is preferably not less than a particular value. When the weight ratio of serine to threonine (serine/threonine) is not less than a particular value, the composition of the present invention can exhibit a desired effect (e.g., peripheral neuropathic pain relieving effect etc.) sufficiently.

Specifically, the weight ratio of serine to threonine (serine/threonine) is preferably not less than 2.60, more preferably not less than 5.20, particularly preferably not less than 10.40.

The weight ratio of serine to threonine (serine/threonine) is a value obtained by dividing the amount of serine in the composition of the present invention by the amount of threonine in the present invention. The amount of threonine in the composition of the present invention is calculated as a total weight of threonine in any form contained in the composition of the present invention. When the form of threonine is other than a free form, for example, salt or amino acid constituting peptide and protein, and the like, the weight of the threonine is converted to the weight of a free form.

The weight ratio of serine and threonine (serine/threonine) contained in 100 g of a food edible part in a natural food material is shown in the following Table 1 (calculated based on "STANDARD TABLES OF FOOD COMPOSITION IN JAPAN: AMINO ACID COMPOSITION OF FOODS 2010" (the Subdivision on Resources, the Council for Science and Technology, Ministry of Education, Culture, Sports, Science and Technology, Japan) which is incorporated herein by reference in its entirety). As shown in Table 1, a food having a weight ratio of serine to threonine (serine/threonine) of not less than 2.60 cannot be realized with a natural food material. Such food requires addition of, for example, serine in a free form and the like to a natural food material.

TABLE 1

|  | serine/threonine |
| --- | --- |
| raw milk (Holstein) | 1.15 |
| rice (milled rice) | 1.48 |
| sweet potato (tuberous root, raw) | 0.97 |
| soybean (dried) | 1.33 |
| onions (bulb, raw) | 1.50 |
| apples (raw) | 1.20 |
| Shiitake mushroom (raw) | 0.92 |
| Wakame (salted) | 0.89 |
| jack mackerel (raw) | 0.85 |
| pacific saury (raw) | 0.90 |
| Shiba shrimp (raw) | 0.94 |
| beef, comminuted meat (raw) | 0.85 |
| pork, comminuted meat (raw) | 0.89 |
| chicken, leg (with skin, raw) | 0.92 |
| egg of hen, whole egg (raw) | 1.57 |

The upper limit of the weight ratio of serine to threonine (serine/threonine) is not particularly limited, a smaller amount of threonine is more preferable, and the composition of the present invention is most preferably substantially free of threonine. The weight ratio of threonine to serine (threonine/serine, i.e., value obtained by dividing the amount of threonine in the composition of the present invention by the amount of serine in the present invention) is preferably not more than 0.38, more preferably not more than 0.20, particularly preferably not more than 0.10, most preferably 0. Being "substantially free of" threonine here means either (a)

completely free of threonine, or (b) containing threonine in an amount not influential on the effect of the composition of the present invention (e.g., not more than 1 wt %, preferably not more than 0.1 wt %, relative to the total amount of amino acid).

In addition, since even threonine taken from meals and the like (e.g., threonine contained in protein etc.) may influence the effect of the composition of the present invention, ingestion of the composition of the present invention and the ingestion of threonine (e.g., meal etc.) are preferably at least 1 hour (preferably not less than 2 hours) apart.

The total amount amino acid contained in the composition of the present invention is generally 1 to 90 wt %, preferably 5 to 85 wt %, relative to the whole composition.

Lipid Comprising n-3 Fatty Acid

The lipid used in the composition of the present invention essentially contains n-3 fatty acid. The term "n-3 fatty acid" in the present specification means an unsaturated fatty acid having a double bond at the third from the terminal methyl group of the hydrocarbon chain, and specific examples thereof include eicosapentaenoic acid, docosahexaenoic acid, α-linolenic acid, docosapentaenoic acid, and the like. The n-3 fatty acid used in the composition of the present invention is preferably eicosapentaenoic acid, docosahexaenoic acid or docosapentaenoic acid, particularly preferably eicosapentaenoic acid. These n-3 fatty acids may be used alone, or two or more kinds thereof may be used in combination.

In the present specification, eicosapentaenoic acid is sometimes to be abbreviated as "EPA".

The n-3 fatty acid is abundantly contained in fats and oils such as fish oil, Japanese basil oil, flaxseed oil and the like, and n-3 fatty acid extracted and purified from these fats and oils can be used. In addition, n-3 fatty acid produced by a method known per se (e.g., chemical synthesis method, fermentation method etc.) can also be used. A commercially available product marketed for foods can also be used. In addition, fats and oils abundantly containing n-3 fatty acid can also be used directly.

The lipid contained in the composition of the present invention may contain n-3 fatty acid as well as other lipids. Examples of the lipid include edible vegetable oils such as cottonseed oil, sunflower oil, peanuts oil, rapeseed oil, soybean oil, safflower oil, olive oil, rice oil, corn oil, sesame oil, cacao butter and the like; edible animal oils such as beef tallow, lard, fish oil, butter, butter oil and the like; processed fat and oils such as shortening and the like; middle chain fatty acid oils such as coconut oil, palm oil, palm kernel oil and the like, and the like. These lipids may be used alone, or two or more kinds thereof may be used in combination.

The amount of n-3 fatty acid is preferably not less than 20 wt %, more preferably not less than 25 wt %, particularly preferably not less than 30 wt %, relative to the total amount of lipid contained in the composition of the present invention.

The upper limit of the amount of n-3 fatty acid is not particularly limited.

When n-3 fatty acid contains eicosapentaenoic acid, the content of eicosapentaenoic acid relative to the total amount of n-3 fatty acid is generally 5 to 100 wt %, based on the total weight of n-3 fatty acid. To suppress oil intake as much as possible, it is preferably 10 to 100 wt %, more preferably 50 to 100 wt %, based on the total weight of n-3 fatty acid.

The total amount of lipid contained in the composition of the present invention is generally 1 to 90 wt %, preferably 5 to 85 wt %, relative to the whole composition.

The composition of the present invention can be provided as a medicament and the like. When provided as a medicament, the subject of administration is, for example, a mammal (e.g., human, mouse, rat, hamster, rabbit, cat, dog, bovine, sheep, monkey etc.) and the like, preferably human.

When the composition of the present invention is provided as a medicament, the dosage form thereof is not particularly limited, and may be any of oral medicament and parenteral medicament. Examples of the oral medicament include tablet, granule, powder, capsule (including soft capsule), elixir, syrup, microcapsule, drink, emulsion, suspension and the like, and examples of the parenteral medicament include skin external preparation (e.g., ointment, cream, gel, liquid, lotion, facial mask, bathing powder etc.), injection and the like. The composition can also be used in combination with analgesic (opioid central analgesic; steroid; non-steroidal antiphlogistic analgetic and the like) commercially available at present.

Serine and n-3 fatty acid, which are active ingredients of the composition of the present invention, can be each singly or combinedly contained in plural (two or more) compositions. The plural compositions may be, for example, a combination of two or more medicaments and the like.

When serine and n-3 fatty acid are contained in plural compositions, the amount of serine relative to the total amount of amino acid, the amount of n-3 fatty acid relative to the total amount of lipid, the content of eicosapentaenoic acid relative to the total amount of n-3 fatty acid and the like are calculated from the total amount of each component contained in plural compositions.

The composition of the present invention may contain carriers conventionally used in the field of medicament and the like as necessary, as long as the object of the present invention is not impaired.

When the composition of the present invention is an oral medicament and the like, examples of the carrier that may be contained include binders such as tragacanth, gum arabic, cornstarch, gelatin, high molecular weight polyvinylpyrrolidone and the like; excipients such as cellulose and a derivative thereof (e.g., microcrystalline cellulose, crystalline cellulose, hydroxypropyl cellulose etc.) and the like; swelling agents such as cornstarch, pregelatinized starch, alginic acid, dextrin and the like; lubricants such as magnesium stearate and the like; flowability improving agents such as particle silicon dioxide, methyl cellulose and the like; lubricants such as glycerin fatty acid ester, talc, polyethylene glycol 6000 and the like; thickeners such as sodium carboxymethyl cellulose, carboxyvinyl polymer, xanthan gum, gelatin and the like; sweetening agents such as sucrose, lactose, aspartame and the like; flavors such as peppermint flavor, vanilla flavor, cherry flavor, orange flavor and the like; emulsifiers such as monoglyceride, polyglycerin fatty acid ester, sucrose fatty acid ester, lecithin, polyoxyethylene hydrogenated castor oil, polyoxyethylene monostearic acid ester and the like; pH adjusters such as citric acid, sodium citrate, acetic acid, sodium acetate, sodium hydroxide and the like; thickeners such as sodium carboxymethyl cellulose, carboxyvinyl polymer, xanthan gum, gelatin and the like; corrigents such as aspartame, licorice extract, saccharin and the like; antioxidants such as erythorbic acid, butylated hydroxyanisole, propyl gallate and the like; preservatives such as sodium benzoate, sodium edetate, sorbic acid, sodium sorbate, methyl p-hydroxybenzoate, butyl p-hydroxybenzoate and the like; colorants such as red iron oxide, yellow iron oxide, black iron oxide, carmine, Food Color Blue No. 1, Food Color Yellow No. 4, Food Color Red No. 2 and the like; fats and oils; antioxidants such as vitamin C, vitamin A, vitamin E, various polyphenol, hydroxytyrosol, antioxidant amino acid and the like; coating agents such as shellac, sugar, hydroxypropyl methylcellulose phthalate, polyacetin and the like; preservatives such as methylparaben, propylparaben and the like; various vitamins; various amino acids and the like.

When the composition of the present invention is a parenteral medicament and the like, examples of the carrier that may be contained include higher fatty acid esters such as petrolatum, liquid paraffin, isopropyl myristate, octyldodecyl myristate and the like; higher alcohols such as squalane, lanolin, cetanol and the like; grease bases such as silicone oil, oil from plant or animal and the like; lower alcohols such as ethanol and the like; polyvalent alcohols such as polyethylene glycol, propylene glycol and the like; emulsifiers or emulsion stabilizers such as α-monoglyceryl ether, lecithin, sorbitan ester of fatty acid, dextrin fatty acid ester, fatty acid monoglyceride, fatty acid metal salt, magnesium sulfate and the like; aromatic; preservative; dye; thickener; antioxidant; UV defense agent; wound therapeutic agent; anti-inflammatory agent; moisturizer; water and the like.

The composition of the present invention can be formulated as a unit package form per single intake. In the present specification, the "unit package form per single intake" means a package form of one or more units with single intake as one unit. For the package, a packaging material and a packaging method, a filling method (e.g., divided package, stick package etc.) generally used for a package of medicament and the like can be used.

In the present specification, the "single intake" is, for example, the amount of the composition to be administered at one time when the composition of the present invention is a medicament. The single intake can be appropriately controlled according to the age, body weight, sex and the like of the subject who ingests.

A single intake of the composition of the present invention can be appropriately set according to the form, dosage form, ingestion subject and the like of the composition and is not particularly limited. For a general adult (body weight 60 kg), 0.2 to 12.0 g is preferable, 0.3 to 10.0 g is more preferable, and 0.5 to 8.0 g is particularly preferable. When the single intake of the composition of the present invention is within the above-mentioned range, it does not influence general meals much, and a sustained ingestion is expected.

The composition of the present invention in a unit package form per single intake preferably contains not less than 0.1 g (more preferably not less than 0.2 g, particularly preferably not less than 0.3 g) of serine in one unit. The content of serine in this case is preferably not more than 10.0 g (more preferably not more than 8.0 g, particularly preferably not more than 5.0 g) in one unit. When the content is less than 0.1 g in one unit, serine is utilized as a protein constituting component or energy source in the body and a desired effect tends to be unexpected. When the content exceeds 10.0 g in one unit, a large amount of a single amino acid is ingested, which is not very preferable from the aspect of amino acid balance.

When the composition of the present invention is in a unit package form per single intake, the content of threonine is preferably not more than 0.15 g (more preferably not more than 0.1 g, further preferably not more than 0.05 g, particularly preferably not more than 0.025 g), in one unit.

When the composition of the present invention is in a unit package form per single intake, n-3 fatty acid is preferably contained at not less than 0.03 g (more preferably not less than 0.04 g, particularly preferably not less than 0.05 g) in one unit. In this case, the content of n-3 fatty acid is preferably not more than 6.00 g (more preferably not more than 4.50 g, particularly preferably not more than 3.00 g) in one unit. When the content is less than 0.03 g in one unit, a desired effect tends to be not clearly expected. A content exceeding 6.00 g in one unit is not very preferable from the aspect of flavor.

When the composition of the present invention is a unit package form per single intake and n-3 fatty acid contains eicosapentaenoic acid, it contains eicosapentaenoic acid at preferably 20 to 4000 mg, more preferably 30 to 3000 mg, particularly preferably 40 to 2000 mg, in one unit.

While the daily intake of serine can be appropriately set according to the age, sex, body weight, meal state and the like of the subject who ingests, it is generally 0.1 to 10.0 g, preferably 0.2 to 8.0 g, more preferably 0.3 to 5.0 g, for an ordinary adult (body weight 60 kg).

In addition, ingestion of not less than 2 g of n-3 fatty acid per day is recommended in Japan for an ordinary adult (body weight 60 kg) based on the lipid ingestion state in the past.

Ingestion of not less than 1 g of eicosapentaenoic acid concurrently with docosahexaenoic acid per day is recommended in Japan for an ordinary adult (body weight 60 kg) based on the lipid ingestion state in the past.

The composition of the present invention is preferably ingested once to several times per day (preferably 1 to 3 times per day), so that the daily intake of serine, n-3 fatty acid and eicosapentaenoic acid will each fall within the above-mentioned ranges.

For application of the composition of the present invention to an animal other than human, the above-mentioned single intake, content in one unit, daily intake and the like can be appropriately increased or reduced based on the above-mentioned amount for an ordinary adult, and further considering the body weight or size of the animal, or the condition, sensitivity and the like of the animal at the time of administration.

For application of the composition of the present invention to a human, the dose of each component (serine etc.) in the composition of the present invention can be determined based on the experiment results of each animal other than human. For example, when a dose for a human is estimated from the experiment results using rats, it can be assumed that the intake per body weight of rat is the same as the intake per body weight of human. Therefore, for example, since ingestion of L-serine at 10.5 mg/body weight kg by rat is described in the below-mentioned Examples, an intake of L-serine by an ordinary adult (body weight 60 kg) is calculated to be 630 mg based on the description. Similarly, based on the description of ingestion of L-threonine at 2.0 mg/body weight kg to rat, an intake of L-threonine by an ordinary adult (body weight 60 kg) is calculated to be 120 mg.

The composition of the present invention can be produced by a method known per se in the technical field of preparation formulation (e.g., the method described in the Japanese Pharmacopoeia, 16th Edition, which is incorporated herein by reference in is entirety, and the like).

The composition of the present invention is useful for the prophylaxis or improvement of peripheral neuropathy. Particularly, it is useful for relieving hypersensitive pain in peripheral neuropathy. Also, it is useful for the prophylaxis or improvement of activity decline due to peripheral neuropathy.

The composition of the present invention is useful for the prophylaxis or improvement of peripheral neuropathy due to an anticancer agent. Peripheral neuropathy due to an anticancer agent is developed in the body of patients as the anticancer agent attacks cancer. A treatment with an anticancer agent sometimes needs to be stopped due to the sustained pain throughout the body. The composition of the present invention is useful for a continuous treatment with anticancer agent and the like, since it can relieve peripheral neuropathic pain due to anticancer agents.

While anticancer agent is not particularly limited as long as it can induce peripheral neuropathy, examples thereof include taxane anticancer agents such as paclitaxel, docetaxel and the like; platinum complex anticancer agents such as oxaliplatin, cisplatin, carboplatin and the like; vinca alkaloid anticancer agents such as vincristine and the like; alkylating anticancer agents such as ifosfamide and the like; antimetabolic anticancer agents such as methotrexate, fluorouracil, cytarabine and the like; antibiotic anticancer agents such as doxorubicin, bleomycin and the like; and the like.

The composition of the present invention is useful for the prophylaxis or improvement of peripheral neuropathy due to knee osteoarthritis. In addition, the composition of the present invention is useful for the prophylaxis or improvement of disuse syndrome. Knee osteoarthritis is developed at high frequency in elderly women, and is a representative example of locomotive syndrome. Since knee osteoarthritis accompanies strong pain as the stage advances, it reduces activity of patients (e.g., elderly people etc.) and weakens the muscles of leg and loin. As a result, a still more burden is placed on the knees to further exacerbate gonarthrosis, and disuse syndrome is developed, thus forming a negative spiral. Moreover, a decrease in the opportunity to go out for elderly people also influences depression, dementia, continuation of independent life and the like. Since the composition of the present invention can relieve the pain of knee joint, it is useful for escaping from the aforementioned negative spiral and the like.

Peripheral neuropathic pain occurs due to abnormality of sensory neuron that transmits signals of sensory organs in the extremities and the like. The cell body of sensory neuron is present in the dorsal spinal root ganglion, and transmits stimulus signals by extending nerve fibers to the terminals of the extremities and the like and interior of the spinal cord. When an abnormality in the sensory neuron occurs, abnormality such as excessive depolarization and the like occurs in a site where information of the dorsal spinal root ganglion and the interior of the spinal cord are integrated and the like, as a result of which hypersensitive pain occurs in various parts of the body. Examples of the disease associated with such peripheral neuropathic, hypersensitive pain include backbone neuropathy (e.g., hernia of intervertebral disk, lumbar spinal stenosis, spondylosis deformans etc.), peripheral neuropathy due to mechanical compression of peripheral nerve trunk, diabetic peripheral neuropathy, renal disease uremic peripheral neuropathy, peripheral neuropathy due to herpes zoster, Guillain-Barre syndrome and the like. The composition of the present invention is preferably used for these peripheral neuropathic pains.

When a pain is developed only in one limb, the limb with the developed pain tends to show decreased motor activity. On the other hand, since the other limb tries to compensate for the decreased motor activity, the motor activity tends to increase. As a result, the muscle balance between right and left limbs collapses, and the physical ability sometimes decreases. Such change in the muscle balance, and decrease in the physical ability can occur not only by the above-mentioned peripheral neuropathic pain due to knee osteoarthritis, but also by limb arthralgia due to sports, rheumatism, gout and the like. The composition of the present invention is preferably used for such change in the muscle balance and decrease in the physical ability.

The present invention also provides a method for the prophylaxis or improvement of peripheral neuropathy, comprising administering an effective amount of the composition of the present invention to a subject in need thereof, and a method for the prophylaxis or improvement of activity decline due to peripheral neuropathy, comprising administering an effective amount of the composition of the present invention to a subject in need thereof.

These methods may exclude a medical practice. The "medical practice" here means an act of treating, operating on or diagnosing human, which is performed by physicians or dentists, or under instruction and supervision of physicians or dentists.

Other features of the invention will become apparent in the course of the following descriptions of exemplary embodiments which are given for illustration of the invention and are not intended to be limiting thereof.

EXAMPLES

Example 1. Granular Powder Nutrition Composition 1

Respective components shown in Table 2 were mixed in a compact high-speed mixer (NSK-150S, manufactured by OKADA SEIKO CO., LTD.) for 5 minutes. Thereafter, to the mixture were added distilled water and 99.5% alcohol at 2 to 5 wt %, and the mixture was kneaded in the mixer for 5 minutes to give a moistened kneaded mixture. The moistened kneaded mixture was granulated by an extrusion granulator with a 1.0 mm$_\varphi$ screen, and the obtained formed product was dried at normal pressure, 70° C. for 2 hours and sieved and 1.05 g of the granule was filled in an aluminum bag. The thus-obtained granular powder nutrition composition 1 was preserved at 24° C. for one year. All components were stably present even after the preservation. The granular powder nutrition composition 1 could be used by mixing with a nutritional supplement dissolved in warm water, and could also be formulated as ion drinks. Furthermore, the composition was mixed with spice, salts such as sodium chloride and the like, sodium glutamate, nucleic acid and the like, and the mixture could be added to various foods.

TABLE 2

| | mixing ratio (wt %) | |
|---|---|---|
| | Example 1-1 | Example 1-2 |
| L-serine | 62 | 32 |
| powdered fish oil (containing 9.5 wt % EPA, containing 20.7 wt % n-3 fatty acid) | 33.1 | 63.1 |
| sucrose ester of fatty acid | 2.85 | 2.85 |
| flavor preparation | 0.95 | 0.95 |
| Lecithin | 1.1 | 1.1 |
| 99.5% alcohol | — | — |
| distilled water | — | — |
| total amount | 100 | 100 |

Example 2. Granular Powder Nutrition Composition 2

In the same manner as in Example 1 except that kneading was performed by a mortar instead of the high-speed mixer, and a horizontal extruder (manufactured by limited company UMETANI iron factory) was used as the extrusion granulator, granular powder nutrition composition 2 was obtained.

Example 3. Liquid Composition-Filled Capsule Product

Respective components shown in Table 3 were mixed and filled in a soft capsule made of a plant-derived coating film to the total weight of 343.747 mg, and packed in an aluminum bag. The thus-obtained liquid compositions (Examples 2-1, 2-2) were preserved under 24° C., humidity 78% conditions for one year. All components were stably present even after the preservation.

TABLE 3

|  | mixing ratio (wt %) | |
| --- | --- | --- |
|  | Example 2-1 | Example 2-2 |
| L-serine | 45.5 | 11.0 |
| fish oil (containing 28 wt % EPA, containing 40 wt % n-3 fatty acid) | 45.5 | 80.0 |
| plant-derived fats and oils | 2.1 | 2.1 |
| Beeswax | 6.7 | 6.7 |
| plant lecithin | 0.2 | 0.2 |
| total amount | 100 | 100 |

Experimental Example 1. Evaluation of Hypersensitive Pain Relieving Effect of the Composition of the Present Invention in Rat Having Hypersensitive Pain Induced by Anticancer Agent The relieving effect of the composition of the present invention on hypersensitive pain by anticancer agent was studied by the following experiment.

6-Week-old male SD rats were divided into 5 groups (1A group-1E group, N=6) based on the body weight, an anticancer agent (Oxaliplatin 5 mg/body weight kg) was intraperitoneally administered to 4 groups other than 1A group for 5 days, and saline was intraperitoneally administered to 1A group for 5 days. In addition, the following evaluation liquid was orally ingested once per day in the time zone of 4 to 5 hours after start of the light period for 28 days simultaneously from the start of the intraperitoneal administration. As eicosapentaenoic acid administered to 1D group, 1E group, fish oil corresponding to 300 mg/body weight kg (equivalent to 429 mg/body weight kg as n-3 fatty acid) was used.

Evaluation Liquids for 1A Group-1E Group:
1A group: distilled water
1B group: distilled water
1C group: L-serine 10.5 mg/body weight kg
1D group: eicosapentaenoic acid 300 mg/body weight kg equivalent
1E group: L-serine 10.5 mg/body weight kg+eicosapentaenoic acid 300 mg/body weight kg equivalent Von Frey test was performed at 22 days and 28 days after the start of the anticancer agent administration. Von Frey test was performed by observing the presence or absence of a foot withdrawing reaction (pain response) when a filament with a different size (stimulation intensity: 4 g, 8 g, 15 g) was pressed against the center part of the sole of foot at right angle at a given speed. Each filament was pressed against the right and left feet 5 times each, totaling 10 times. The interval of pressing was 5 minutes. The ratio (%) of the number of pain response relative to the number (10 times) of filament pressing was calculated at each stimulation intensity.

Figure 2:
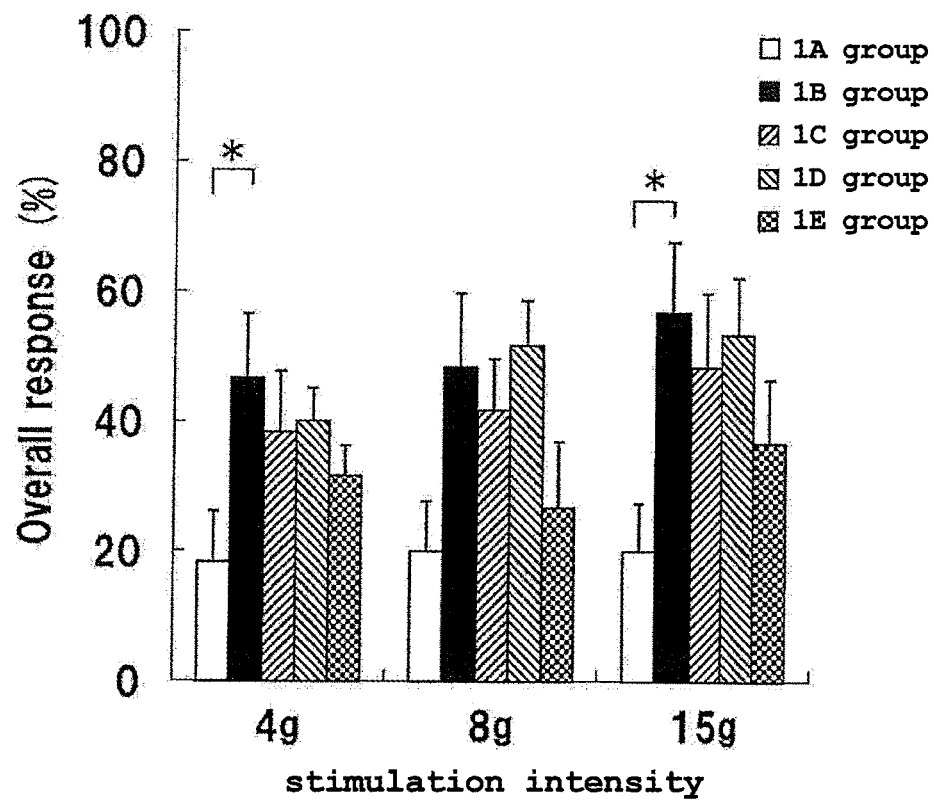
FIG. 2 shows the results of Von Frey test at 28 days after the start of the administration of an anticancer agent in Experimental Example 1. * shows the presence of a significant difference ($p<0.05$, non-paired t-test) as compared to 1B group. The vertical axis (Overall response (%)) shows the ratio (%) of the number of pain response relative to the number of pressing of a filament.

The test results at 22 days after the start of the anticancer agent administration are shown in FIG. 1, and the test results at 28 days after the start of the anticancer agent administration are shown in FIG. 2.

As is clear from the test results of FIG. 1 and FIG. 2, since the number of pain response of 1B group increased than 1A group both at 22 days and 28 days after the start of the anticancer agent administration, induction of hypersensitive pain by the anticancer agent was confirmed.

In the serine single administration group (1C group), the number of pain response slightly decreased as compared to 1B group at any stimulation intensity, and a hypersensitive pain relieving effect was observed, though the level thereof was not significant.

In the eicosapentaenoic acid single administration group (1D group), the number of pain response hardly changed as compared to 1B group at any stimulation intensity.

In the serine and eicosapentaenoic acid combined administration group (1E group), the number of pain response remarkably decreased as compared to 1B group, and a significant hypersensitive pain relieving effect was observed.

From the above-mentioned test results, it was considered that the combined use administration of serine and n-3 fatty acid can efficiently relieve hypersensitive pain by anticancer agent.

Experimental Example 2. Evaluation of Hypersensitive Pain Relieving Effect of the Composition of the Present Invention in Rat Having Hypersensitive Pain Induced by Gonitis Inducing Agent (Zymosan)

The relieving effect of the composition of the present invention on hypersensitive pain in gonitis was studied by the following experiment.

8-Week-old male SD rats were divided into 5 groups (2A group-2E group, N=7) based on the body weight, and 2 mg of a gonitis inducing agent (Zymosan) was administered to the right knee cartilage part in 4 groups other than 2A group. In addition, the following evaluation liquid was orally ingested once per day in the time zone of 4 to 5 hours after start of the light period for 21 days from the administration of the gonitis inducing agent to the right knee. As eicosapentaenoic acid administered to 2D group, 2E group, fish oil corresponding to 300 mg/body weight kg (equivalent to 429 mg/body weight kg as n-3 fatty acid) was used.

Evaluation Liquids for 2A Group-2E Group:
2A group: distilled water
2B group: distilled water
2C group: L-serine 10.5 mg/body weight kg
2D group: eicosapentaenoic acid 300 mg/body weight kg equivalent
2E group: L-serine 10.5 mg/body weight kg+eicosapentaenoic acid 300 mg/body weight kg equivalent Von Frey test was performed at 7 days and 14 days after the gonitis inducing agent administration. Von Frey test was performed by observing the presence or absence of a foot withdrawing reaction (pain response) when a filament with a different size (stimulation intensity: 4 g, 8 g, 15 g) was pressed against the center part of the sole of foot at right angle at a given speed. Each filament was pressed against the right and left feet 5 times each. The interval of pressing was 5 minutes. The ratio (%) of the number of pain response relative to the number (5 times) of filament pressing was calculated at each stimulation intensity.

Figure 3:
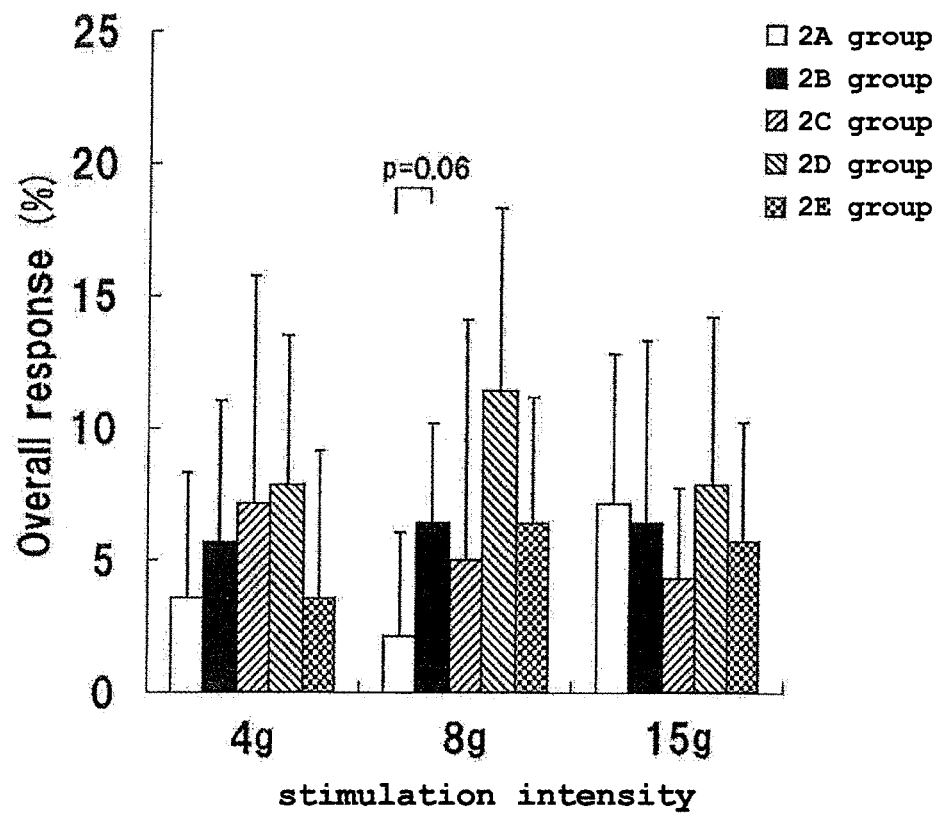
FIG. 3 shows the results of Von Frey test of the right foot at 7 days after the administration of a gonitis inducing agent in Experimental Example 2. The vertical axis (Overall response (%)) shows the ratio (%) of the number of pain response relative to the number of pressing of a filament.
Figure 4:
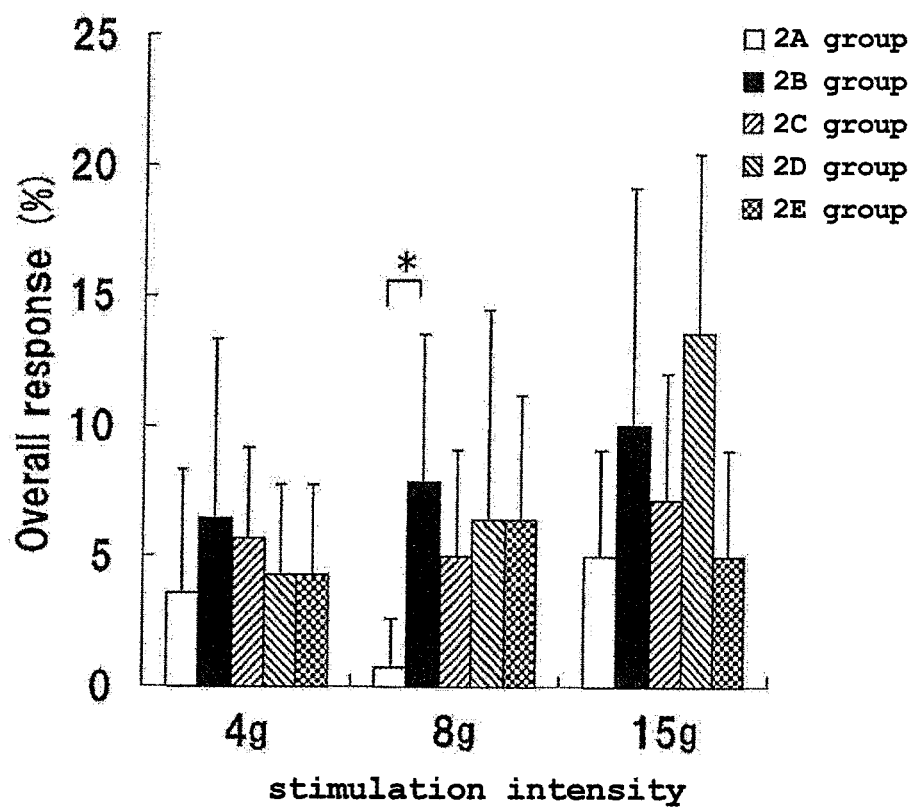
FIG. 4 shows the results of Von Frey test of the left foot at 7 days after the administration of a gonitis inducing agent in Experimental Example 2. * shows the presence of a significant difference ($p<0.05$, non-paired t-test) as compared to 2B group. The vertical axis (Overall response (%)) shows the ratio (%) of the number of pain response relative to the number of pressing of a filament.
Figure 5:
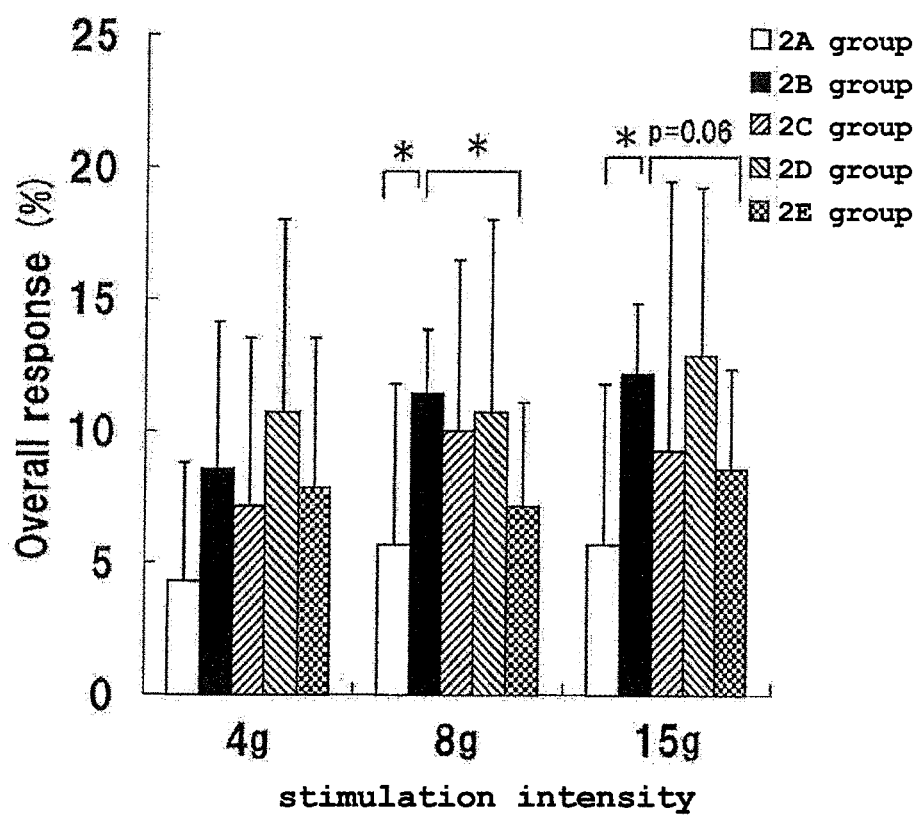
FIG. 5 shows the results of Von Frey test of the right foot at 14 days after the administration of a gonitis inducing agent in Experimental Example 2. * shows the presence of a significant difference ($p<0.05$, non-paired t-test) as compared to 2B group. The vertical axis (Overall response (%)) shows the ratio (%) of the number of pain response relative to the number of pressing of a filament.
Figure 6:
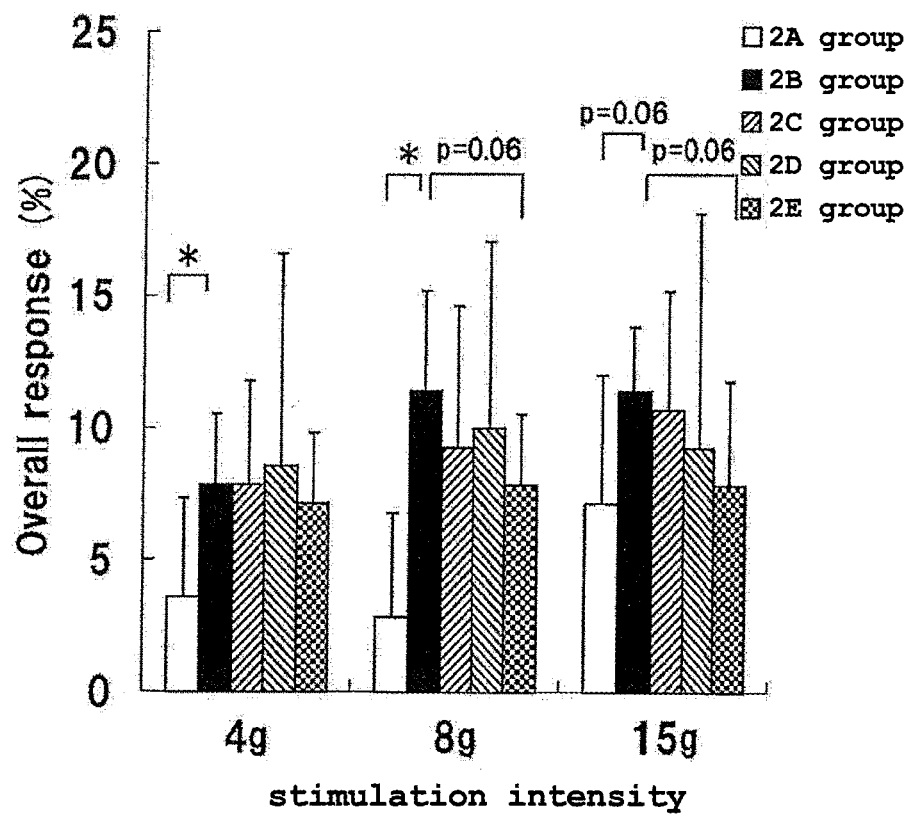
FIG. 6 shows the results of Von Frey test of the left foot at 14 days after the administration of a gonitis inducing agent in Experimental Example 2. * shows the presence of a significant difference ($p<0.05$, non-paired t-test) as compared to 2B group. The vertical axis (Overall response (%)) shows the ratio (%) of the number of pain response relative to the number of pressing of a filament.

The test results of the right foot at 7 days after the gonitis inducing agent administration are shown in FIG. 3, and the test results of the left foot are shown in FIG. 4. The test results of the right foot at 14 days after the gonitis inducing agent administration are shown in FIG. 5, and the test results of the left foot are shown in FIG. 6.

Figure 7:
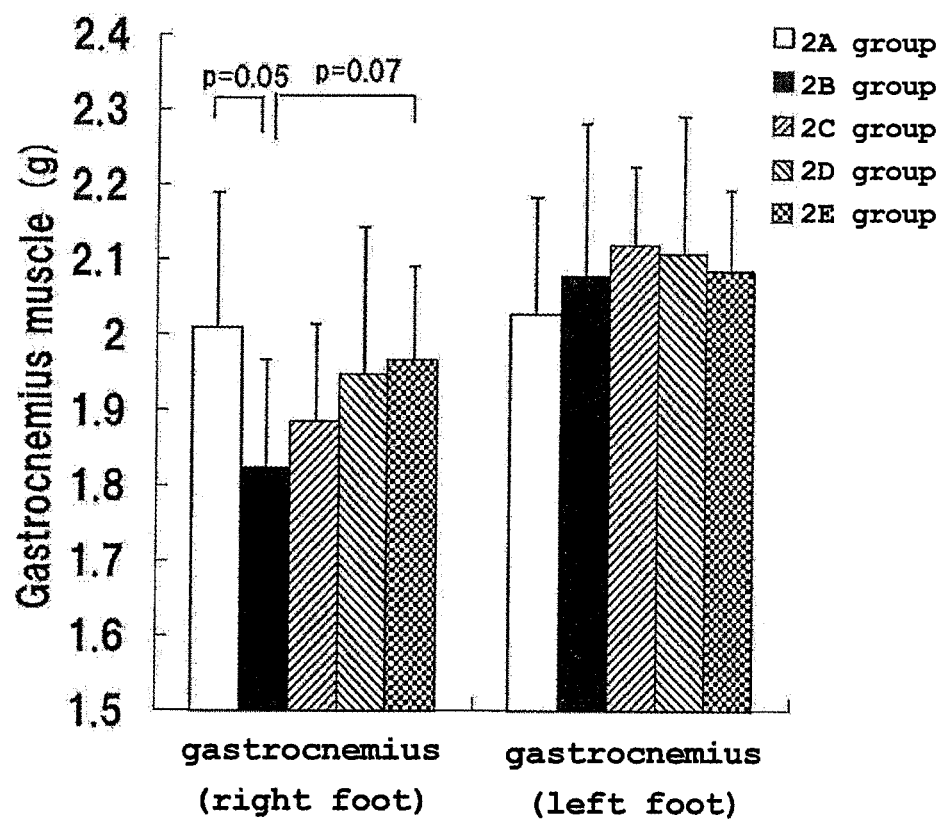
FIG. 7 shows the measurement results of the gastrocnemius weight of the right foot and left foot in Experimental Example 2. The vertical axis (Gastrocnemius muscle (g)) shows the weight (g) of the gastrocnemius.
Figure 8:
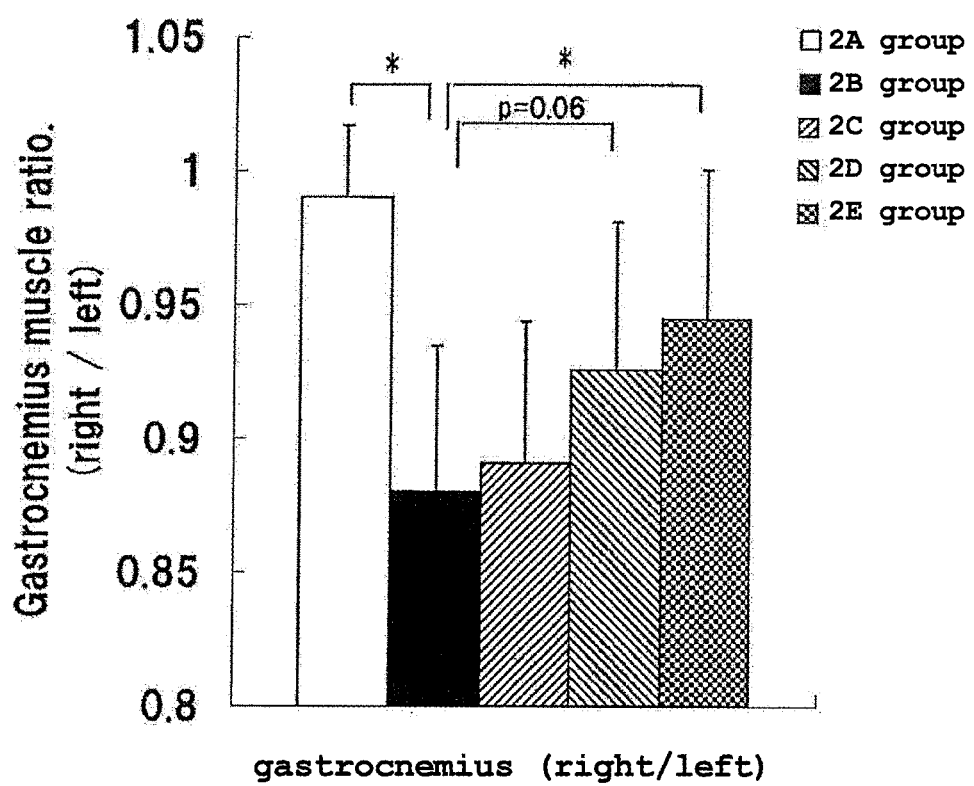
FIG. 8 shows the ratio of the gastrocnemius weight of the right foot and the gastrocnemius weight of the left foot (right foot/left foot) in Experimental Example 2. * shows the presence of a significant difference ($p<0.05$, non-paired t-test) as compared to 2B group. The vertical axis (Gastrocnemius muscle ratio.) shows the ratio of the gastrocnemius weight of the right foot and the gastrocnemius weight of the left foot (right foot/left foot).

After the completion of ingestion of the evaluation liquid (21 days after gonitis inducing agent administration), rats were fasted for 17 hours, and the body weight, gastrocnemius weight of the right foot and the left foot, liver weight and weight of fat around epididymis of each group were measured. The measurement results of the gastrocnemius weight of the right foot and the left foot are shown in FIG. 7. The ratio of the gastrocnemius weights of the right foot and the left foot (right foot/left foot) is shown in FIG. 8.

As is clear from the test results of FIGS. 3 to 6, the number of pain response of 2B group significantly increased than 2A group not only in the right foot administered with the gonitis inducing agent but also in the left foot, both at 7 days and 14 days after the start of the evaluation liquid administration (i.e., 7 days and 14 days after the gonitis inducing agent administration).

In the L-serine single administration group (2C group), the number of pain response slightly decreased as compared to 2B group at any stimulation intensity, and a hypersensitive pain relieving effect was observed, though the level thereof was not significant.

In the eicosapentaenoic acid single administration group (2D group), the number of pain response hardly changed as compared to 2B group at any stimulation intensity.

In the L-serine and eicosapentaenoic acid combined administration group (2E group), the number of pain response remarkably decreased as compared to 2B group. Particularly, at 14 days after the gonitis inducing agent administration, a significant decrease in the number of pain response or a decrease tendency thereof was found in both feet at stimulation intensity 8 g and 15 g.

As is clear from the measurement results of FIG. 7, the gastrocnemius weight of the right foot of the groups (2B group-2E group) administered with the gonitis inducing agent showed a decreasing tendency as compared to the group (2A group) free of the gonitis inducing agent administration. A comparison of the gastrocnemius weight of the right foot in the 2C group to 2E group reveals that it was highest in 2E group, next high in 2D group, and lowest in 2C group. Since the groups administered with the gonitis inducing agent dragged the right foot along, the gastrocnemius weight of the left foot in those groups showed an increase tendency as compared to the groups free of the gonitis inducing agent administration. The difference between the gastrocnemius weight of the right foot and that of the left foot was the largest in 2B group, and a difference of not less than 10% was found. By comparison of the difference among 2C group to 2E group in the gastrocnemius weight of both feet, the difference was largest in 2C group, next large in 2D group, and smallest in 2E group. Particularly, it was confirmed that the balance of gastrocnemius of the right foot and gastrocnemius of the left foot was significantly recovered in 2E group.

The body weight, liver weight and weight of fat around epididymis did not show a significant difference between respective groups.

From the above-mentioned test results, it was considered that the action to relieve hypersensitive pain by anticancer agent and the action to relieve hypersensitive pain in gonitis by the combined use administration of serine and n-3 fatty acid do not result from a single effect afforded by each component, but a synergistic effect afforded by the combined use of serine and n-3 fatty acid. Thus, the usefulness of a combined use of serine and n-3 fatty acid was shown in mammals including rat.

Experimental Example 3. Evaluation of Influence of Threonine on Hypersensitive Pain Relieving Effect of the Composition of the Present Invention in Rat Having Induced Hypersensitive Pain An influence of threonine addition on the hypersensitive pain relieving effect of the composition of the present invention was studied by the following experiment.

8-Week-old male SD rats were divided into 6 groups (3A group-3F group, N=6) based on the body weight, and 2 mg of a gonitis inducing agent (Zymosan) was administered to the right knee cartilage part in 5 groups other than 3A group. In addition, the following evaluation liquid was orally ingested once per day in the time zone of 4 to 5 hours after start of the light period from the next day of the administration of the gonitis inducing agent to the right knee. As eicosapentaenoic acid administered to 3C group to 3F group, fish oil corresponding to 100 mg/body weight kg (equivalent to 143 mg/body weight kg as n-3 fatty acid) was used. In addition, as shown below, in 3C group to 3F group, the dose of L-serine was fixed at 10 mg/body weight kg, and the dose of L-threonine was changed in 0.8 to 8.1 mg/body weight kg.

Evaluation Liquids for 3A Group-3F Group:
 3A group: distilled water
 3B group: distilled water
 3C group: L-serine 10.5 mg/body weight kg+/0 eicosapentaenoic acid 100 mg/body weight kg equivalent+L-threonine 8.1 mg/body weight kg (L-serine/L-threonine=1.30)
 3D group: L-serine 10.5 mg/body weight kg+eicosapentaenoic acid 100 mg/body weight kg equivalent+L-threonine 4.1 mg/body weight kg (L-serine/L-threonine=2.56)
 3E group: L-serine 10.5 mg/body weight kg+eicosapentaenoic acid 100 mg/body weight kg equivalent+L-threonine 2.0 mg/body weight kg (L-serine/L-threonine=5.25)
 3F group: L-serine 10.5 mg/body weight kg+eicosapentaenoic acid 100 mg/body weight kg equivalent+L-threonine 0.8 mg/body weight kg (L-serine/L-threonine=13.13)

Von Frey test was performed at 21 days after the gonitis inducing agent administration. Von Frey test was performed by observing the presence or absence of a foot withdrawing reaction (pain response) when a filament with a different size (stimulation intensity: 4 g, 8 g, 15 g) was pressed against the center part of the sole of foot at right angle at a given speed. Each filament was pressed against the right foot 5 times. The interval of pressing was 5 minutes. The ratio (%) of the number of pain response relative to the number (5 times) of filament pressing was calculated at each stimulation intensity.

Figure 9:
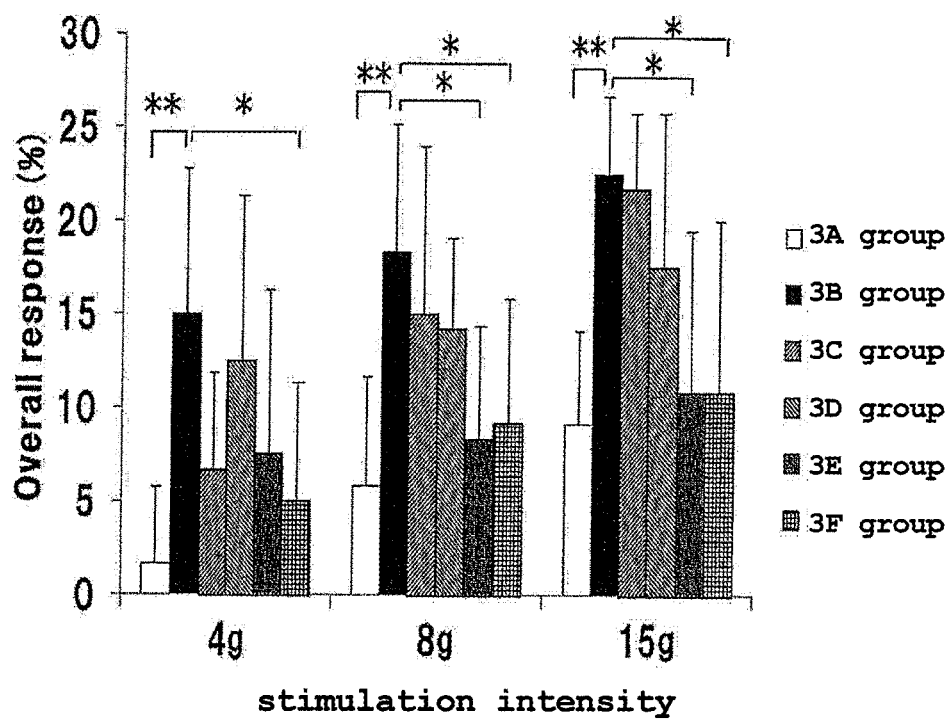
FIG. 9 shows the results of Von Frey test of the right foot at 21 days after the administration of a gonitis inducing agent in Experimental Example 3. ** and * show the presence of a significant difference (**:$p<0.01$, *:$p<0.05$, non-paired t-test) as compared to 3B group. The vertical axis (Overall response (%)) shows the ratio (%) of the number of pain response relative to the number of pressing of a filament.

The test results of the right foot at 21 days after the gonitis inducing agent administration are shown in FIG. 9.

As shown in FIG. 9, the number of pain response of 3B group administered with the gonitis inducing agent showed a significant increase as compared to 3A group.

Of 3C to 3F groups with varying dose of L-threonine, the number of pain response of 3C group and 3D group did not show a significant decrease as compared to 3B group at any stimulation intensity. However, 3E group and 3F group showed a significant decrease at many stimulation intensities. That is, when the weight ratio of L-serine to L-threonine (L-serine/L-threonine) was not more than 2.56, hypersensitive pain relieving effect was not found, and the relieving effect was found at not less than 5.25 where the ratio of L-serine is higher.

From the above-mentioned test results, it was clarified that a weight ratio of serine to threonine (serine/threonine) exceeding 2.56 is preferable for sufficient exhibition of the hypersensitive pain relieving effect of the composition of the present invention containing threonine.

Experimental Example 4. Evaluation of Influence of Meal on Hypersensitive Pain Relieving Effect of the Composition of the Present Invention in Rat Having Induced Hypersensitive Pain An influence of meal on the hypersensitive pain relieving effect of the composition of the present invention was studied by the following experiment.

8-Week-old male SD rats were divided into 5 groups (4A group-4E group, N=6) based on the body weight, and 2 mg of a gonitis inducing agent (Zymosan) was administered to the right knee cartilage part in 4 groups other than 4A group. In addition, the following evaluation liquid was orally ingested once per day in the following administration time zone from the next day of the administration of the gonitis inducing agent to the right knee. The amount of L-serine taken by 4C group to 4E group was 10 mg/body weight kg, and as EPA (eicosapentaenoic acid), fish oil corresponding to 100 mg/body weight kg (equivalent to 143 mg/body weight kg as n-3 fatty acid) was used. Each group had a meal simultaneously with the start of the dark period every day, and the amount of threonine ingested by one meal was 313 mg/body weight kg as a free form. The amount of serine ingested by one meal was 489 mg/body weight kg as a free form, and the weight ratio of serine to threonine (serine/threonine) in the meal was 1.56.

Evaluation Liquids and Administration Time Zones for 4A Group to 4F Group:
  4A group: distilled water/administered at 9 hr from the start of light period
  4B group: distilled water/administered at 9 hr from the start of light period
  4C group: L-serine+EPA/administered at 9 hr from the start of light period
  4D group: L-serine+EPA/administered immediately before meal
  4E group: L-serine+EPA/administered at 1 hr from meal Von Frey test was performed at 14 days after the gonitis inducing agent administration. Von Frey test was performed by similar steps as in Experimental Example 3. The test results of the right foot at 14 days after the gonitis inducing agent administration are shown in FIG. 10.

Figure 10:
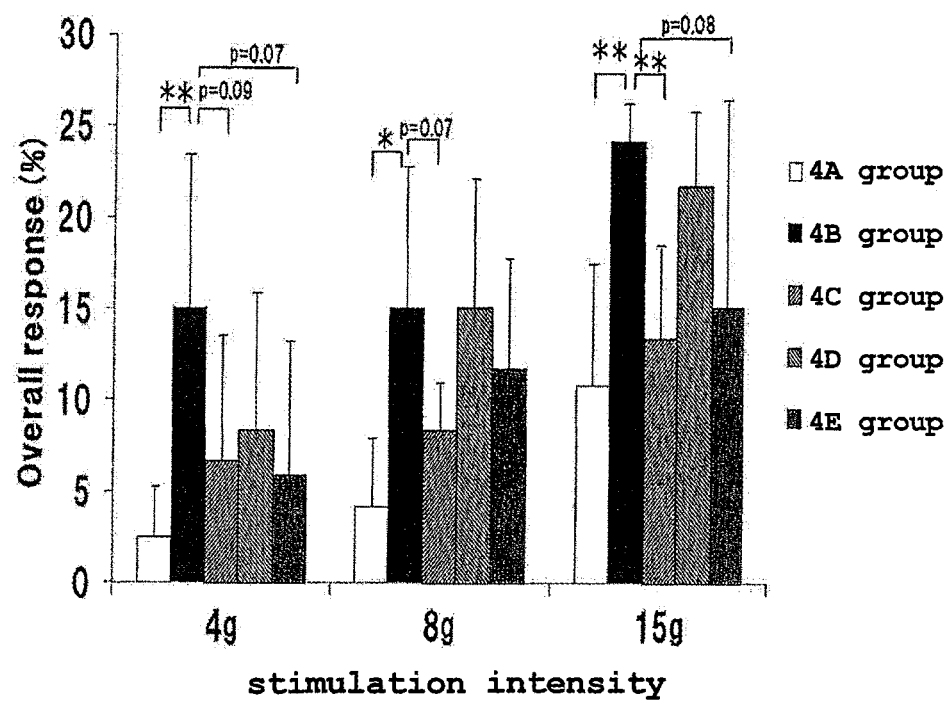
FIG. 10 shows the results of Von Frey test of the right foot at 14 days after the administration of a gonitis inducing agent in Experimental Example 4. ** and * show the presence of a significant difference (**:$p<0.01$, *:$p<0.05$, non-paired t-test) as compared to 4B group. The vertical axis (Overall response (%)) shows the ratio (%) of the number of pain response relative to the number of pressing of a filament.

As shown in FIG. 10, the number of pain response of 4B group administered with the gonitis inducing agent showed a significant increase as compared to 4A group.

In 4C group with administration of L-serine and EPA at 9 hr from the start of light period, which is a time zone not less than 3 hr apart from the meal immediately before, a significant decrease in the number of pain response or a decrease tendency thereof was found as compared to 4B group. On the other hand, in 4D group with administration immediately before the meal, a significant decrease was not found as compared to 4B group, and the number of pain response increased as compared to 4C group. Furthermore, in 4E group with administration at 1 hr after the meal, a significant decrease in the number of pain response or a decrease tendency thereof was found as compared to 4B group; however, when compared to 4C group, the number of pain response increased at stimulation intensity of 8 g and 15 g.

From the above-mentioned test results, it was assumed that the administration of the composition of the present invention at least 1 hr from the meal is preferable, and a longer time from the meal is more preferable, for sufficient exhibition of the hypersensitive pain relieving effect of the composition of the present invention containing threonine.

Experimental Example 5. Influence of the Composition of the Present Invention on Behavior Amount in Rat Having Induced Hypersensitive Pain An influence of the composition of the present invention on behavior amount was studied by the following experiment.

8-Week-old male SD rats were divided into 3 groups (5A group-5C group, N=6) based on the body weight, and 2 mg of a gonitis inducing agent (Zymosan) was administered to the right knee cartilage part in 2 groups other than 5A group. In addition, the following evaluation liquid was orally ingested once per day in the time zone of 4 to 5 hours after start of the light period from the next day of the administration of the gonitis inducing agent to the right knee. As eicosapentaenoic acid administered to 5C group, fish oil corresponding to 100 mg/body weight kg (equivalent to 143 mg/body weight kg as n-3 fatty acid) was used.

Evaluation Liquids for 5A Group-5C Group]:
  5A group: distilled water
  5B group: distilled water
  5C group: L-serine 10.5 mg/body weight kg+eicosapentaenoic acid 100 mg/body weight kg equivalent At 7 days and 14 days after the gonitis inducing agent administration, the behavior amount was measured for a whole day by a behavior amount measuring apparatus using an infrared sensor (SUPERMEX, manufactured by Muromachi Kikai Co., Ltd.). The behavior amount measurement results of the dark period (12 hr) at 7 days and 14 days later are shown in FIG. 11.

Figure 11:
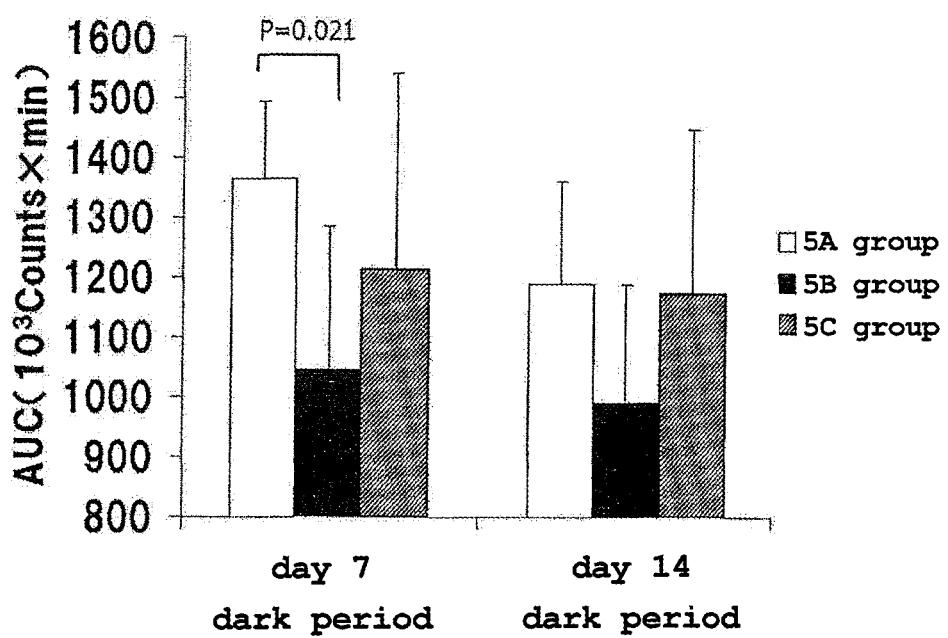
FIG. 11 shows the measurement results of the behavior amount of 5A group-5C group in Experimental Example 5. The vertical axis (AUC ($10^3$ Countsxmin)) shows the accumulated number of passage of infrared sensor by the rats in the cage.

As shown in FIG. 11, the behavior amount of 5B group was found to be lower than 5A group both at 7 days and 14 days after the gonitis inducing agent administration. In 5C group, a decrease in the behavior amount was suppressed to about 50% of the decrease in 5B group, at 7 days after the gonitis inducing agent administration, and the behavior amount at 14 days later was found to have recovered to the same value as in 5A group.

From the above-mentioned test results, it was clarified that the composition of the present invention relieves hypersensitive pain, and further recovers the decreased behavior amount.

INDUSTRIAL APPLICABILITY

According to the present invention, the composition for the prophylaxis or improvement of peripheral neuropathy can be provided. Particularly, the composition provides an effect of relieving peripheral neuropathic pain, and is useful for peripheral neuropathy due to administration of anticancer agents, peripheral neuropathy due to knee osteoarthritis, backbone neuropathy (e.g., hernia of intervertebral disk, lumbar spinal stenosis, spondylosis deformans etc.), peripheral neuropathy due to mechanical compression of peripheral nerve trunk, diabetic peripheral neuropathy, renal disease uremic peripheral neuropathy, peripheral neuropathy due to herpes zoster and Guillain-Barre syndrome and the like. The composition can also prevent or improve activity decline due to peripheral neuropathy. Furthermore, since the composition contains L-serine and n-3 fatty acid with established safety as active ingredients, it can be ingested safely for a long term, and can enhance the QOL of the subject who ingests.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for the improvement of peripheral neuropathy, comprising administering to a subject in need thereof an effective amount of a composition comprising at least one amino acid comprising serine, and at least one lipid comprising eicosapentaenoic acid.

2. The method according to claim 1, wherein said serine is present in said composition in an amount of not less than 50 wt % relative to the total amount of amino acid in said composition.

3. The method according to claim 1, wherein said composition: (1) is substantially free of threonine; or (2) has a weight ratio of serine relative to threonine of not less than 2.60.

4. The method according to claim 1, wherein the amount of said eicosapentaenoic acid in said composition is not less than 20 wt % relative to the total amount of said at least one lipid in said composition.

5. The method according to claim 1, wherein said composition is administered in a unit package form for single intake, and comprises not less than 0.1 g of serine in one unit and not less than 0.03 g of eicosapentaenoic acid in one unit.

6. The method according to claim 1, wherein said peripheral neuropathy is one or more selected from the group consisting of peripheral neuropathy due to an anticancer agent, peripheral neuropathy due to knee osteoarthritis, backbone neuropathy, peripheral neuropathy due to mechanical compression of peripheral nerve trunk, diabetic peripheral neuropathy, renal disease uremic peripheral neuropathy, peripheral neuropathy due to herpes zoster, and Guillain-Barre syndrome.

7. The method according to claim 1, wherein said peripheral neuropathy is peripheral neuropathy due to an anticancer agent or peripheral neuropathy due to knee osteoarthritis.

8. A method for the prophylaxis or improvement of activity decline due to peripheral neuropathy, comprising administering to a subject in need thereof an effective amount of a composition comprising at least one amino acid comprising serine, and at least one lipid comprising eicosapentaenoic acid.

9. The method according to claim 8, wherein said serine is present in said composition in an amount of not less than 50 wt % relative to the total amount of amino acid in said composition.

10. The method according to claim 8, wherein said composition: (1) is substantially free of threonine; or (2) has a weight ratio of serine relative to threonine of not less than 2.60.

11. The method according to claim 8, wherein the amount of said eicosapentaenoic acid in said composition is not less than 20 wt % relative to the total amount of said at least one lipid in said composition.

12. The method according to claim 8, wherein said composition is administered in a unit package form for single intake, and comprises not less than 0.1 g of serine in one unit and not less than 0.03 g of eicosapentaenoic acid in one unit.

13. The method according to claim 8, wherein said peripheral neuropathy is one or more selected from the group consisting of peripheral neuropathy due to an anticancer agent, peripheral neuropathy due to knee osteoarthritis, backbone neuropathy, peripheral neuropathy due to mechanical compression of peripheral nerve trunk, diabetic peripheral neuropathy, renal disease uremic peripheral neuropathy, peripheral neuropathy due to herpes zoster, and Guillain-Barre syndrome.

14. The method according to claim 8, wherein said peripheral neuropathy is peripheral neuropathy due to an anticancer agent or peripheral neuropathy due to knee osteoarthritis.

* * * * *